United States Patent
Murphy et al.

(10) Patent No.: US 10,150,719 B2
(45) Date of Patent: Dec. 11, 2018

(54) PRODUCTION OF 1,6-HEXANEDIOL FROM ADIPIC ACID

(71) Applicant: Archer-Daniels-Midland Company, Decatur, IL (US)

(72) Inventors: Vincent J. Murphy, San Jose, CA (US); Eric L. Dias, Belmont, CA (US); James A. W. Shoemaker, Gilroy, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 14/913,730

(22) PCT Filed: Aug. 22, 2014

(86) PCT No.: PCT/US2014/052345
§ 371 (c)(1),
(2) Date: Feb. 23, 2016

(87) PCT Pub. No.: WO2015/027184
PCT Pub. Date: Feb. 26, 2015

(65) Prior Publication Data
US 2016/0200646 A1    Jul. 14, 2016

Related U.S. Application Data

(60) Provisional application No. 61/869,554, filed on Aug. 23, 2013.

(51) Int. Cl.
| | |
|---|---|
| *C07C 29/149* | (2006.01) |
| *B01J 37/08* | (2006.01) |
| *B01J 37/18* | (2006.01) |
| *B01J 23/652* | (2006.01) |
| *B01J 23/656* | (2006.01) |

(52) U.S. Cl.
CPC ......... *C07C 29/149* (2013.01); *B01J 23/6525* (2013.01); *B01J 23/6527* (2013.01); *B01J 23/6567* (2013.01); *B01J 37/08* (2013.01); *B01J 37/18* (2013.01)

(58) Field of Classification Search
None
See application file for complete search history.

(56) References Cited

U.S. PATENT DOCUMENTS

| | | | | |
|---|---|---|---|---|
| 4,937,058 A | * | 6/1990 | Dupin | C01B 17/508 423/224 |
| 5,969,194 A | | 10/1999 | Hara et al. | |
| 6,204,417 B1 | | 3/2001 | Fischer et al. | |
| 6,495,730 B1 | * | 12/2002 | Konishi | B01J 21/18 568/831 |
| 2010/0317822 A1 | | 12/2010 | Boussie et al. | |
| 2010/0317823 A1 | * | 12/2010 | Boussie | B01J 23/40 528/323 |

FOREIGN PATENT DOCUMENTS

WO    2013163540 A1    10/2013

OTHER PUBLICATIONS

He et al. Tetrahedron Letters, 36(7), 1059-1062, 1995.*
J-Plat Pat machine translation of JP 53-033567 B with Espacenet Bibliographic Data, 5 pages.

* cited by examiner

*Primary Examiner* — Clinton A Brooks
(74) *Attorney, Agent, or Firm* — Stinson Leonard Street LLP

(57) ABSTRACT

Processes are disclosed for the conversion of adipic acid to 1,6-hexanediol employing a chemocatalytic reaction in which an adipic acid substrate is reacted with hydrogen in the presence of particular heterogeneous catalysts including a first metal and a second metal on a support. The adipic acid substrate includes adipic acid, mono-esters of adipic acid, di-esters of adipic acid, and salts thereof. The first metal is selected form the group of Pt, Rh and mixtures thereof and the second metal is selected from the group of Mo, W, Re and mixtures thereof.

22 Claims, No Drawings

PRODUCTION OF 1,6-HEXANEDIOL FROM ADIPIC ACID

REFERENCE TO RELATED APPLICATIONS

This application is a United States National Stage Application of International Application No. PCT/US2014/052345, filed Aug. 22, 2014, and claims the benefit of U.S. Provisional Application No. 61/869,554, filed Aug. 23, 2013, the entire disclosures of which are incorporated herein by reference.

FIELD OF INVENTION

The present disclosure relates generally to processes for the chemocatalytic conversion of an adipic acid substrate to 1,6-hexanediol; more specifically, it relates to chemocatalytic conversion of an adipic acid substrate, preferably adipic acid, to 1,6-hexanediol via a reaction with hydrogen in the presence of particular heterogeneous catalysts.

BACKGROUND

Most commodity and specialty organic chemicals used in the manufacture of polymers and other materials are derived from crude oil. For example, 1,6-hexanediol, one such chemical, is used as a starting material for polyesters, polyurethanes, and diacrylates, among others.

1,6-hexanediol has been made by processes in which cyclohexane, a hydrocarbon produced from steam cracking of oil, is initially converted to the carboxylic acid adipic acid or epsilon-hydroxycaprioc acid, the carboxylic acid is then esterified with an alcohol, and the resulting ester is reacted with hydrogen in the presence of a hydrogenation catalyst. This process is recognized as being disadvantageous because of the esterification step and because the hydrogenation reaction is conducted under high temperature and pressure. See, for example, JP-B-53-33567 which employs a copper hydrogenation catalyst in such a process.

Several processes have been disclosed for the production of 1,6-hexanediol from those same carboxylic acids, which processes do not include an esterification step. Those processes disclose the use of a variety of catalysts including cobalt, rhenium and Raney nickel. However, those processes employ relatively severe reaction conditions and/or suffer from unsatisfactory catalyst performance. Other processes have been disclosed which convert a salt of a carboxylic acid directly to the diol but, similarly to the acid conversion processes, the reaction conditions are extreme because of the use of cobalt catalysts.

Mitsubishi has reported the direct hydrogenation of a mixture of adipic acid and hydroxycaproic acid to 1,6-hexanediol using catalysts containing ruthenium, tin and platinum. See, for example, U.S. Pat. No. 5,969,194. However, the temperatures and pressures employed in the exemplified processes are economically undesirable and, thus, do not suggest a commercially viable process.

There remains a need for processes for the production of 1,6-hexanediol which do not suffer from the deficiencies of the prior art.

SUMMARY

Briefly, therefore, the present invention is directed to preparing 1,6-hexanediol from an adipic acid substrate which, preferably, may be obtained from biorenewable materials. Generally, the process for preparing 1,6-hexanediol from an adipic acid substrate comprises chemocatalytically converting an adipic acid substrate to 1,6-hexanediol by reacting the substrate with hydrogen in the presence of particular heterogeneous catalysts.

In one aspect, the present invention is directed to a process for preparing 1,6-hexanediol, the process comprising:

reacting an adipic acid substrate and hydrogen in the presence of a heterogeneous catalyst comprising first metal selected from the group consisting of Pt, Rh, and mixtures thereof and second metal selected from the group consisting of Mo, W, Re, and mixtures thereof to convert at least a portion of the adipic acid substrate to 1,6-hexanediol, wherein the adipic acid substrate is a compound of formula I:

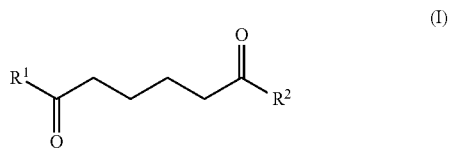

wherein each $R^1$ and $R^2$ is independently hydroxyl or $OR^a$; and wherein each $R^a$ is independently selected from the group consisting of alkyl and a salt-forming ion. In some embodiments, the reacting the adipic acid substrate with hydrogen in the presence of the heterogeneous catalyst comprises:

a) combining the adipic acid substrate, heterogeneous catalyst, and a solvent; and, b) contacting the combined adipic acid substrate, heterogeneous catalyst, and solvent with hydrogen. In other embodiments, the reacting the adipic acid substrate with hydrogen in the presence of the heterogeneous catalyst comprises:

a) combining the adipic acid substrate and a solvent; and, b) contacting the combined adipic acid substrate and solvent with a heterogeneous catalyst and hydrogen. In other embodiments, the reacting the adipic acid substrate with hydrogen in the presence of the heterogeneous catalyst and a solvent comprises:

a) combining the adipic acid substrate, heterogeneous catalyst, and a solvent at a temperature in the range of from about 20° C. to about 200° C.; and b) contacting with hydrogen the combined adipic acid substrate, heterogeneous catalyst, and solvent. In other embodiments, the reacting the adipic acid substrate with hydrogen in the presence of the heterogeneous catalyst comprises:

a) contacting the heterogeneous catalyst with hydrogen;

b) adding the adipic acid substrate and a solvent to the heterogeneous catalyst contacted with hydrogen. In other embodiments, the reacting the adipic acid substrate with hydrogen in the presence of the heterogeneous catalyst and solvent comprises:

a) contacting the heterogeneous catalyst with a solvent at a temperature in the range of from about 20° C. to about 200° C.; and b) contacting the heterogeneous catalyst and solvent with the adipic acid substrate and hydrogen. In other embodiments, the reacting the adipic acid substrate with hydrogen in the presence of the heterogeneous catalyst and solvent comprises:

a) contacting the adipic acid substrate with water; and,
b) contacting the adipic acid substrate and water with a solvent, hydrogen, and catalyst.

In some embodiments that can be combined with any of the previous embodiments, the adipic acid substrate is derived from a carbohydrate source. In other embodiments that can be combined with any of the previous embodiments, the adipic acid substrate is selected from the group consisting of adipic acid, a mono-ester of adipic acid, a di-ester of adipic acid, or salts thereof. In some embodiments that can be combined with any of the previous embodiments, the heterogeneous catalyst comprises a support selected from the group consisting of $Al_2O_3$, $TiO_2$, $ZrO_2$, $SiO_2$, zeolites, carbon, and mixtures thereof. In other embodiments that can be combined with any of the previous embodiments, the support consists essentially of $SiO_2$ or $ZrO_2$. In some embodiments that can be combined with any of the previous embodiments, the solvent is selected from the group of water, ethers, alcohols which do not react with the adipic acid substrate, and mixtures thereof. In some embodiments that can be combined with any of the previous embodiments, the total concentration of the first metal and the second metal is at least about 0.1 wt. % to about 20 wt. % of the total weight of the catalyst. In other embodiments that can be combined with any of the previous embodiments, the total concentration of the first metal and the second metal is at least about 0.1 wt. % to about 10 wt. % of the total weight of the catalyst. In other embodiments that can be combined with any of the previous embodiments, the total concentration of the first metal and the second metal is at least about 0.2 wt. % to about 10 wt. % of the total weight of the catalyst. In other embodiments that can be combined with any of the previous embodiments, the total concentration of the first metal and the second metal is at least about 0.2 wt. % to about 8 wt. % of the total weight of the catalyst. In other embodiments that can be combined with any of the previous embodiments, the total concentration of the first metal and the second metal is at least about 0.2 wt. % to about 6 wt. % of the total weight of the catalyst. In other embodiments that can be combined with any of the previous embodiments, the total concentration of the first metal and the second metal is equal to or less than about 6 wt. % of the total weight of the catalyst and the total weight of the second metal is at least about 0.2 wt. % of the total weight of the catalyst. In other embodiments that can be combined with any of the previous embodiments, the concentration of the second metal is at least about 0.2 wt. % of the total weight of the catalyst and the concentration of the first metal is at least about 2 wt. % of the total weight of the catalyst. In some embodiments that can be combined with any of the previous embodiments, the molar ratio of the first metal to the second metal (M1:M2) is in the range of from about 10:1 to about 1:5. In other embodiments that can be combined with any of the previous embodiments, the molar ratio of the first metal to the second metal (M1:M2) is in the range of from about 10:1 to about 1:3. In other embodiments that can be combined with any of the previous embodiments, the molar ratio of the first metal to the second metal (M1:M2) is in the range of from about 10:1 to about 1:2. In other embodiments that can be combined with any of the previous embodiments, the molar ratio of the first metal to the second metal (M1:M2) is in the range of from about 10:1 to about 2:1. In other embodiments that can be combined with any of the previous embodiments, the molar ratio of the first metal to the second metal (M1:M2) is in the range of from about 10:1 to about 3:1. In some embodiments that can be combined with any of the previous embodiments, the total concentration of the first metal and the second metal is at least about 0.1 wt. % to about 20 wt. % of the total weight of the catalyst and the molar ratio of the first metal to the second metal is in the range of from about 10:1 to about 1:5. In other embodiments that can be combined with any of the previous embodiments, the total concentration of the first metal and the second metal is at least about 0.2 wt. % to about 6 wt. % of the total weight of the catalyst and the molar ratio of the first metal to the second metal (M1:M2) is in the range of from about 10:1 to about 3:1. In some embodiments that can be combined with any of the previous embodiments, the first metal is Pt and the second metal is selected from Mo, W and mixtures thereof. In other embodiments that can be combined with any of the previous embodiments, the second metal is Mo and W. In some embodiments that can be combined with any of the previous embodiments, the reaction is carried out at a pressure in the range of about 200 psig (1480 kPa) to about 3000 psig (20786 kPa). In other embodiments that can be combined with any of the previous embodiments, the reaction is carried out at a pressure in the range of about 400 psig (2859 kPa) to about 1200 psig (8375 kPa). In other embodiments that can be combined with any of the previous embodiments, the reaction is carried out at a pressure in the range of about 400 psig (2859 kPa) to about 1000 psig (6996 kPa). In other embodiments that can be combined with any of the previous embodiments, the reaction is carried out at a partial pressure of hydrogen in the range of from about 200 psi (1379 kPa) to about 2500 psi (17237 kPa). In other embodiments that can be combined with any of the previous embodiments, the reaction is carried out at a partial pressure of hydrogen in the range of from about 500 psig (3549 kPa) to about 1500 psig (10443 kPa). In other embodiments that can be combined with any of the previous embodiments, the reaction is carried out at a partial pressure of hydrogen in the range of from about 650 psig (4583 kPa) to about 1250 psig (8720 kPa). In some embodiments that can be combined with any of the previous embodiments, the reaction is carried out at a temperature in the range of from about 20° C. to about 300° C. In other embodiments that can be combined with any of the previous embodiments, the reaction is carried out at a temperature in the range of from about 40° C. to about 200° C. In other embodiments that can be combined with any of the previous embodiments, the reaction is carried out at a temperature in the range of from about 70° C. to about 180° C. In some embodiments that can be combined with any of the previous embodiments, the reaction is carried out at a pressure in the range of from about 200 psig (1480 kPa) to about 2500 psig (17338 kPa) and a temperature in the range of from about 20° C. to about 300° C. In other embodiments that can be combined with any of the previous embodiments, the reaction is carried out at a pressure in the range of from about 650 psig (4583 kPa) to about 1250 psig (8720 kPa) and a temperature in the range of from about 70° C. to about 180° C. In some embodiments that can be combined with any of the previous embodiments, the reaction is carried out at a partial pressure of hydrogen in the range of from about 200 psi (1379 kPa) to about 2500 psi (17237 kPa) and a temperature in the range of from about 20° C. to about 300° C. In other embodiments that can be combined with any of the previous embodiments, the reaction is carried out at a partial pressure of hydrogen in the range of from about 650 psi (4482 kPa) to about 1250 psi (8618 kPa) and a temperature in the range of from about 70° C. to about 180° C. In some embodiments that can be combined with any of the previous embodiments, the heterogeneous catalyst comprises a support having a surface area in the range of from about 20 to about 200 m²/g, and the concentration of the second metal (M2) is in the range of from about 0.1 to about 4 wt. % of the total weight of the catalyst. In some embodiments that can be combined with any of the previous embodiments, the support is zirconia. In some embodiments that can be combined with any of the previous embodiments, the heterogeneous catalyst comprises a support having a surface area in the range of from about 60 to about 600 m²/g, and the concentration of the second metal (M2) is in the range of from about 0.1 to about 5 wt. % of the total weight of the catalyst. In some embodiments that can be combined with any of the previous embodiments, the support is silica. In some embodiments that can be combined with any of the previous embodiments, the yield of 1,6-hexanediol is at least about 60%. In other embodiments that can be combined with any of the previous embodiments, the yield of 1,6-hexanediol is at least about 70%. In some embodiments that can be combined with any of the previous embodiments, the adipic acid substrate is adipic acid.

In another aspect, the present invention is directed to a catalyst for the hydrogenation of a dicarboxylic acid, the catalyst comprising Pt and at least one of Mo and W on a support selected from the group consisting of $SiO_2$, $ZrO_2$, and zeolites. In some embodiments, the catalyst comprises Pt, Mo and W on a support, wherein the molar ratio of Pt:W+Mo is in the range of from about 10:1 to about 2:1. In some embodiments, the metals of the catalyst consist essentially of Pt, Mo and W and the support consists essentially of silica. In some embodiments that can be combined with any of the previous embodiments, the total concentration of the metals is at least about 0.1 wt. % to about 20 wt. % of the total weight of the catalyst. In other embodiments that can be combined with any of the previous embodiments, the total concentration of the metals is at least about 0.1 wt. % to about 10 wt. % of the total weight of the catalyst. In other embodiments that can be combined with any of the previous embodiments, the total concentration of the metals is at least about 0.2 wt. % to about 10 wt. % of the total weight of the catalyst. In other embodiments that can be combined with any of the previous embodiments, the total concentration of the metals is at least about 0.2 wt. % to about 8 wt. % of the total weight of the catalyst. In other embodiments that can be combined with any of the previous embodiments, the total concentration of the metals is at least about 0.2 wt. % to about 6 wt. % of the total weight of the catalyst. In other embodiments that can be combined with any of the previous embodiments, the total concentration of the first metal and the second metal is equal to or less than about 6 wt. % of the total weight of the catalyst and the total weight of the second metal is at least about 0.2 wt. % of the total weight of the catalyst. In other embodiments that can be combined with any of the previous embodiments, the concentration of the second metal is at least about 0.2 wt. % of the total weight of the catalyst and the concentration of the first metal is at least about 2 wt. % of the total weight of the catalyst. In some embodiments that can be combined with any of the previous embodiments, the molar ratio of the first metal to the second metal (M1:M2) is in the range of from about 10:1 to about 1:5. In other embodiments that can be combined with any of the previous embodiments, the molar ratio of the first metal to the second metal (M1:M2) is in the range of from about 10:1 to about 1:3. In other embodiments that can be combined with any of the previous embodiments, the molar ratio of the first metal to the second metal (M1:M2) is in the range of from about 10:1 to about 1:2. In other embodiments that can be combined with any of the previous embodiments, the molar ratio of the first metal to the second metal (M1:M2) is in the range of from about 10:1 to about 2:1. In other embodiments that can be combined with any of the previous embodiments, the molar ratio of the first metal to the second metal (M1:M2) is in the range of from about 10:1 to about 3:1. In some embodiments that can be combined with any of the previous embodiments, the total concentration of the first metal and the second metal is at least about 0.1 wt. % to about 20 wt. % of the total weight of the catalyst and the molar ratio of the first metal to the second metal is in the range of from about 10:1 to about 1:5. In other embodiments that can be combined with any of the previous embodiments, the total concentration of the first metal and the second metal is at least about 0.2 wt. % to about 6 wt. % of the total weight of the catalyst and the molar ratio of the first metal to the second metal (M1:M2) is in the range of from about 10:1 to about 3:1.

DETAILED DESCRIPTION

The following description sets forth exemplary methods, parameters and the like. It should be recognized, however, that such description is not intended as a limitation on the scope of the present invention.

In accordance with the present invention, applicants disclose processes for the chemocatalytic conversion of adipic acid and/or certain derivatives thereof to 1,6-hexanediol. Generally, the processes for producing 1,6-hexanediol comprises chemocatalytically converting an adipic acid substrate to 1,6-hexanediol by reacting the substrate with hydrogen in the presence of a suitable heterogeneous catalyst.

The 1,6-hexanediol prepared in accordance with the disclosed processes may be converted to various other industrially significant chemicals (e.g., polyurethanes, polyesters, diacrylates) according to processes known in the art.

I. Feedstock

The feedstock is selected from among adipic acid and certain derivatives thereof, as more fully described herein below, and preferably is adipic acid. The feedstock may be obtained from conventional processes in which, for example, cyclohexane is produced from the refining (e.g., by steam cracking) of crude oil, the cyclohexane is then oxidized to "KA oil", and the KA oil is oxidized to produce adipic acid. Alternatively, and from a sustainability and anticipated cost perspective more preferably, the feedstock is obtained from polyhydroxyl-containing biorenewable materials (e.g., glucose derived from starch, cellulose or sucrose) by the processes disclosed in U.S. Patent App. Pubs. US2010/0317822 and US2010/0317823, both of which are hereby incorporated by reference in their entireties.

II. Preparation of 1,6-Hexanediol from an Adipic Acid Substrate

Applicants have discovered that an adipic acid substrate of formula I may be converted to 1,6-hexanediol according to the following, overall reaction scheme:

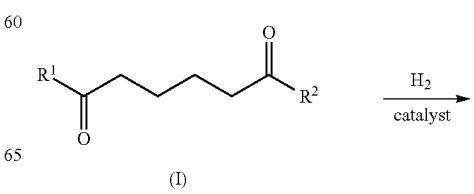

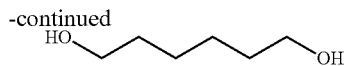

wherein each $R^1$ and $R^2$ is independently hydroxyl or $OR^a$; wherein each $R^a$ is independently selected from the group consisting of alkyl and salt-forming ion. In various embodiments, each $R^1$ and $R^2$ are independently hydroxyl or $OR^a$ wherein each $R^a$ is independently selected from the group consisting of $C_1$-$C_{18}$ alkyl and salt-forming ion. In further embodiments, each $R^1$ and $R^2$ can be independently hydroxyl or $OR^a$ wherein each $R^a$ is independently selected from the group consisting of $C_1$-$C_6$ alkyl and salt-forming ion. As used herein, alkyl refers to a moiety which can be linear, cyclic, or branched. Salt forming ions include, without limitation, for example ammonium ions and metal ions (e.g., alkali and alkaline earth metals). In various preferred embodiments, $R^1$ and $R^2$ are hydroxyl, and the catalyst is selected from among those catalysts described herein below and the process conditions are as more fully described herein below. As illustrated above, the feedstock is an adipic acid substrate of formula I, which includes adipic acid, mono-esters of adipic acid (e.g., $C_1$-$C_{18}$ or $C_1$-$C_6$ mono-esters), di-esters (e.g., $C_1$-$C_{18}$ or $C_1$-$C_6$ di-esters) of adipic acid, or salts (e.g., sodium, potassium, or ammonium salts), or mixtures thereof. An adipic acid ester may be or comprise the substrate first supplied to a reaction zone or may be generated in situ. In various preferred embodiments, the substrate is adipic acid.

III. Catalysts

Metals

Catalysts suitable for this hydrogenation reaction (also generally identified as reduction catalysts) are particular supported heterogeneous catalysts comprising a first metal (M1) selected from the group consisting of Pt, Rh, and mixtures thereof and a second metal (M2) selected from the group consisting of Mo, W, Re and mixtures thereof. In various embodiments, the first metal (M1) is Pt. In other embodiments, the first metal (M1) is Rh. In various embodiments, the second metal (M2) is selected from the group consisting of Mo, W, and mixtures thereof. In some embodiments, the second metal (M2) is Mo. In further embodiments, the second metal (M2) is W. In general, the metals may be present in various forms (e.g., elemental, metal oxide, metal hydroxides, metal ions, alloys, etc.). In various preferred embodiments, the metals are present in elemental form. Also, in various embodiments of the invention, the catalyst may also comprise one or more other metals selected from among d-block metals, rare earth metals (e.g. lanthanides), and/or main group metals (e.g. Al). Typically, the total concentration of the first metal and the second metal (M1+M2) is from about 0.1 wt. % to about 20 wt. %, or from about 0.1 wt. % to about 10 wt. %, or from about 0.2 wt. % to about 10 wt. %, or from about 0.2 wt. % to about 8 wt. %, or from about 0.2 wt. % to about 6 wt. %, of the total weight of the catalyst. In more preferred embodiments the total concentration of the first metal and the second metal (M1+M2) of the catalyst is equal to or less than about 6 wt. % of the total weight of the catalyst and the total weight of the second metal (M2) is at least 0.2 wt. % of the total weight of the catalyst. In some embodiments, the concentration of the second metal is at least about 0.2 wt. %, of the total weight of the catalyst and the concentration of the first metal is at least about 2 wt. % of the total weight of the catalyst. The combination of the first metal(s) (M1) and the second metal(s) (M2) unexpectedly enhance(s) the selectivity and/or activity of the catalyst. Among the second metals, Mo has shown the highest activity while W has demonstrated the highest selectivity. Thus, in preferred embodiments, the M1 metal(s) is (are) selected from the group consisting of Pt, Rh, and mixtures thereof and the M2 metal(s) is(are) selected from among Mo, W, and mixtures thereof. In various preferred embodiments, the M1 metal is Pt and the M2 metal is Mo or W. In combination, these M2 metals appear to provide catalysts with exceptional selectivity and activity and, thus, in certain more preferred embodiments the metals of the catalyst consist essentially of Pt, Mo, and W (excluding the metal component(s) of the inorganic support, if any).

The M1:M2 molar ratio is important. Generally, the molar ratio of M1:M2 is in the range of from about 10:1 to about 1:5. In some embodiments, the ratio is in the range of from about 10:1 to about 1:3, and in other embodiments, the ratio is in the range of from about 10:1 to about 1:2. More typically, the ratio is in the range of from about 10:1 to about 2:1, and still more typically in the range of from about 10:1 to about 3:1. When M1 is Pt or Rh, and M2 is Mo, W, or mixtures thereof the ratio of Pt or Rh:M2 is preferably in the range of from about 10:1 to about 2:1 and more preferably from about 10:1 to about 3:1. In some embodiments, suitable catalysts include catalysts comprising Pt, Mo, and W on a support, wherein the molar ratio of Pt:W+Mo is in the range of from about 10:1 to about 2:1.

All combinations of the first and second metal concentrations and molar ratios of the first and second metal combinations disclosed herein are contemplated. In some embodiments, the total concentration of the first metal and the second metal is at least about 0.1 wt. % to about 20 wt. % of the total weight of the catalyst and the molar ratio of the first metal to the second metal is in the range of from about 10:1 to about 1:5. In various preferred embodiments, the total concentration of the first metal and the second metal is at least about 0.2 wt. % to about 6 wt. % of the total weight of the catalyst and the molar ratio of the first metal to the second metal (M1:M2) is in the range of from about 10:1 to about 3:1.

The ratio of the concentration of the second metal(s) (M2) to the surface area of the support is a further aspect of the invention. For example, for supports (e.g., zirconia supports) having a surface area in the range of about 20 to about 200 $m^2$/g, the concentration of M2 is preferably in the range of from about 0.1 to about 4 wt. % of the total weight of the catalyst. In another example, for supports (e.g., silica supports) having a surface area in the range of about 60 to about 600 $m^2$/g, the concentration of M2 is preferably in the range of from about 0.1 to about 5.0 wt. % of the total weight of the catalyst.

Generally, a sufficient amount of the catalytically active component(s) are available for contact with the adipic acid substrate. Accordingly, in various embodiments, the mass ratio of adipic acid substrate to the M1 metal (i.e., Pt, Rh, and mixtures thereof) is at least about 1:1; at least about 5:1, at least about 7.5:1, or at least about 10:1. The mass ratio of adipic acid substrate to the M1 metal can be in the range of from about 1:1 to about 1000:1, from about 5:1 to about 1000:1, from about 1:1 to about 500:1, from about 5:1 to about 500:1, from about 1:1 to about 200:1, from about 5:1 to about 200:1, from about 7.5:1 to about 100:1, or from about 8:1 to about 60:1. Also, in these and other embodiments, the mass ratio of adipic acid substrate to the M2 metal (i.e., Mo, W, Re, and mixtures thereof) is at least about 5:1, at least about 10:1, at least about 20:1, or at least about 30:1. The mass ratio of adipic acid substrate to the M2 metal can be in the range of from about 5:1 to about 2000:1, from about 10:1 to about 2000:1, from about 10:1 to about 1500:1, from about 20:1 to about 1200:1, from about 30:1 to about 1200:1, or from about 20:1 to about 1000:1. In various embodiments, the mass ratio of adipic acid substrate to the total mass of M1 and M2 (i.e., M1+M2) is typically, at least about 1:1, at least about 5:1, at least about 10:1, at least about 20:1, at least about 30:1, at least about 40:1, or at least about 50:1. The mass ratio of adipic acid substrate to the total mass of M1 and M2 can be in the range from about 1:1 to about 1500:1, from about 5:1 to about 1500:1, from about 20:1 to about 1500:1, from about 20:1 to about 1000:1, from about 30:1 to about 500:1, from about 40:1 to about 500:1, from about 40:1 to about 350:1, or from about 40:1 to about 300:1.

Supports

Catalyst supports useful in combination with the above-described metals to form the heterogeneous, supported catalysts of the present invention can be any of a variety of known supports such as silicas, carbon, zirconias, titanias, aluminas, and zeolites. In various embodiments, the support is selected from among $Al_2O_3$, $TiO_2$, $ZrO_2$, $SiO_2$, and zeolites. In various preferred embodiments, the support is selected from among $SiO_2$, $ZrO_2$, and zeolites. In various preferred embodiments, $SiO_2$ is a particularly effective support material. In other preferred embodiments, $ZrO_2$ is a particularly effective support material. In certain embodiments, M2 may be present as a component of the support: for example, tungstate-modified zirconias have been demonstrated to be effective support materials. The modified support materials may be modified using methods known in the art such for the introduction of a dopant (for example, metal-doped titanias, metal-doped zirconias (e.g., tungstated-zirconia), metal-doped cerias, metal-modified niobias, and mixtures thereof). When modified supports such as tungstated zirconias are employed, the concentration of tungsten is taken into consideration in determining the molar ratio of M1:M2 and with the amount of any separate addition of M2 by the manners described herein.

Catalyst Preparation

Typically, the metals are deposited onto the support using procedures known in the art including, but not limited to incipient wetness, ion-exchange, deposition-precipitation, and vacuum impregnation. In various embodiments, following metal deposition, the catalyst is dried at a temperature in the range of about 20° C. to about 120° C. for a period of time ranging from at least about 1 hour to about 24 hours. In these and other embodiments, the catalyst is dried under sub-atmospheric pressure conditions. In various embodiments, the catalyst is reduced after drying (e.g., by flowing 5% $H_2$ in $N_2$ at a temperature of at least about 200° C. for a period of time e.g., at least about 3 hours). Still further, in these and other embodiments, the catalyst is calcined in air at a temperature of at least about 200° C. and, in many embodiments, up to 600° C. for a period of time of at least about 3 hours. In various embodiments, calcinations are conducted in furnaces using a ramp rate on the order of 4-8° C./min. In various embodiments, the catalyst is reduced and calcined simultaneously. For example, the dried samples may be reduced and calcined by flowing 5% $H_2$ in $N_2$ at a temperature of at least about 200° C. and, in many embodiments, up to 600° C. for a period of time of at least about 3 hours. In various preferred embodiments, the M2 metal is deposited, dried and calcined prior to depositing the M1 metal and, after deposition of the M1 metal, the catalyst is again dried and may be subjected to another calcination step.

In specific embodiments, a metal precursor, such as for example, a metal nitrate (e.g., $Pt(NO_3)_2$ or $Rh(NO_3)_2$) may be dissolved in a solvent, such as, for example, water, to form a first metal precursor solution at a suitable concentration to produce the finished catalyst at the desired metal wt. %. It will be understood that a nitrogen-containing metal precursor is not critical, but other metal precursors may be used, such as metal acetates, metal halides, metal amines, and others. The first metal precursor solution may then be deposited on the support and agitated to impregnate the support. In other specific embodiments, a second metal precursor, such as for example, a molybdate or tungstenate (e.g., $(NH_4)_6Mo_7O_{24}$ or $(NH_4)_6W_{12}O_{41}$), may be dissolved in a solvent, such as, for example, water, to form a second metal precursor solution at a suitable concentration to produce the finished catalyst at the desired metal wt. %. The second metal precursor solution may then be deposited on the support, either sequentially or simultaneously as the first metal precursor solution. Alternatively, in some preferred embodiments, the second metal precursor solution may be deposited, dried, and calcined prior to depositing the first metal precursor solution, and after deposition of the first metal precursor solution, the catalyst is dried, and optionally calcined.

In other specific embodiments, the finished catalyst may be prepared by first drying and calcining a support, followed by deposition of one or more metal solutions onto the calcined support, followed by drying and reducing the supported catalyst. For example, the support material may be synthesized or obtained from commercial sources. The support may first be dried at a temperature in the range of about 20° C. to about 120° C. (e.g., 60° C.) for a period of time ranging from at least about 1 hour to about 24 hours (e.g., overnight or about 12 hours). Then, one or more metal solutions may be impregnated onto the calcined support as described herein, dried, and reduced as described herein.

IV. Reaction Conditions

The hydrogenation reaction can also be conducted in the presence of a solvent. Solvents suitable for use in conjunction with the hydrogenation reaction may include, for example, water, alcohols, esters, ethers, ketones, or mixtures thereof. In various embodiments, the preferred solvent is water.

The order in which the adipic acid substrate, solvent (if any), hydrogen, and catalyst are combined to carry out the conversion of an adipic acid substrate to a 1,6-hexanediol product may vary.

In some embodiments, the adipic acid substrate, the catalyst and solvent can be first combined, before addition of hydrogen. The resulting reaction mixture may then be heated, subjected to appropriate hydrogen partial pressure and other process conditions such as, for example, flow rate of the combined reaction constituents to the reaction zone(s).

In other embodiments, the adipic acid substrate can be contacted with a solvent before introduction of hydrogen. In some variations, the adipic acid substrate may be contacted with a solvent in the presence or absence of the catalyst and/or additional water to the solvent, optionally with heating, and under an atmosphere of air or nitrogen.

In yet other embodiments, the heterogeneous catalyst may first be contacted with hydrogen, before addition of the adipic acid substrate and a solvent.

In yet other embodiments, the heterogeneous catalyst and solvent can be first combined, before addition of the adipic acid substrate and the hydrogen. The catalyst and solvent may be combined at elevated temperature to reduce the catalyst in situ, before addition of the adipic acid substrate and the hydrogen.

In other embodiments, the adipic acid substrate can initially be combined only with water, and then contacted with a solvent, hydrogen, and catalyst. In still other embodiments, the adipic acid substrate can initially be combined with water and thereafter hydrogen, a solvent, and the catalyst may be added.

Generally, the temperature of the reaction mixtures, regardless of the order of addition of reaction constituents, or the conduct of the overall conversion in one or more reactors or reactor zones, is at least about room temperature. Typically, the temperature of the reaction mixture(s) is(are) maintained in the range of from about room temperature (about 20° C.) to about 300° C., and more typically in the range of from about 40° C. to about 200° C. In various preferred embodiments, the temperature(s) is (are) maintained in the range of from about 70° C. to about 180° C.

In some embodiments, the conversion of the adipic acid substrate to 1,6-hexanediol is carried out at a pressure in the range of from about 200 psig (1480 kPa) to about 3000 psig (20786 kPa). In other embodiments, and a pressure in the range of from about 400 psig (2859 kPa) to about 1200 psig (8375 kPa). In other embodiments, and a pressure in the range of from about 400 psig (2859 kPa) to about 1000 psig (6996 kPa). In some embodiments, the disclosed pressure ranges includes the pressure of $H_2$ gas and, optionally an inert gas, such as $N_2$. The partial pressure of hydrogen is typically at least about 200 pounds per square inch (psig) (1480 kPa). In various embodiments, the partial pressure of hydrogen is up to about 2000 psig (13891 kPa). More typically, the partial pressure of hydrogen is in the range of from about 500 psig (3549 kPa) to about 1500 psig (10443 kPa). In many preferred embodiments, the partial pressure of hydrogen is in the range of from about 650 psig (4583 kPa) to about 1250 psig (8720 kPa). In some embodiments, the reaction is carried out under a pressure of hydrogen without any additional inert gas. In many instances, the difference between the reaction pressure and the partial pressure of hydrogen is negligible (on the order of a few atmospheres, or less).

All combinations of temperature ranges and pressure ranges (total pressure and partial pressure of hydrogen and, optionally, an inert gas) disclosed herein to carry out the reaction of an adipic acid substrate to 1,6-hexanediol are contemplated. In some embodiments, the reaction is carried out at a pressure in the range of from about 200 psig (1480 kPa) to about 2500 psig (17338 kPa) and a temperature in the range of from about 20° C. to about 300° C. In various preferred embodiments, the reaction is carried out at a pressure in the range of from about 650 psig (4583 kPa) to about 1250 psig (8720 kPa) and a temperature in the range of from about 70° C. to about 180° C. In some embodiments, the reaction is carried out at a partial pressure of hydrogen in the range of from about 1379 kPa (200 psi) to about 17237 kPa (2500 psi) and a temperature in the range of from about 20° C. to about 300° C. In various preferred embodiments, the reaction is carried out at a partial pressure of hydrogen in the range of from about 650 psi (4482 kPa) to about 1250 psi (8,618 kPa) and a temperature in the range of from about 70° C. to about 180° C.

In general, the hydrogenation reactions can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the adipic acid substrate, hydrogen, any solvent, and the catalyst may be introduced into a suitable reactor separately or in various combinations.

The chemocatalytic conversion of adipic acid substrate to 1,6-hexanediol may yield a mixture of products. In several embodiments, at least 50%, at least 60%, or at least 70% of the product mixture is 1,6-hexanediol. In several embodiments, the production of 1,6-hexanediol from adipic acid is at least about 60%.

The product mixture may be separated into one or more products by any suitable methods known in the art. In some embodiments, the product mixture can be separated by fractional distillation under subatmospheric pressures. For example, in some embodiments, 1,6-hexanediol can be separated from the product mixture at a temperature between about 90° C. and about 110° C. The 1,6-hexanediol may be recovered from any remaining other products of the reaction mixture by one or more conventional methods known in the art including, for example, solvent extraction, crystallization, or evaporative processes.

When introducing elements of the present invention or the preferred embodiments(s) thereof, the articles "a", "an" are intended to be the singular unless the context admits otherwise and "the" and "said" are intended to mean that there are one or more of the elements. The terms "comprising", "including" and "having" are not intended to be inclusive and use of such terms mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Reactions were conducted in 1 mL glass vials housed in a pressurized vessel in accordance with the procedures described in the examples below.

Example 1: Adipic Acid to 1,6-Hexanediol using Pt/Mo Catalysts

Suitably concentrated aqueous solutions of $Pt(NO_3)_2$+ $(NH_4)_6Mo_7O_{24}$ were added to approximately 10 mg of solids and agitated to impregnate the supports. The samples were dried in an oven at 60° C. overnight under a dry air purge. The samples were reduced at 350° C. under forming gas (5% $H_2$ and 95% $N_2$) atmosphere for 3 hours with 5° C./min temperature ramp rate. The final catalysts were composed of ca. 3.9 wt. % Pt and 0.4 wt. % Mo.

These catalysts were tested for adipic acid reduction using the following catalyst testing protocol. Catalyst (ca. 10 mg) was weighed into a glass vial insert followed by addition of an aqueous adipic acid solution (200 µl of 0.1 M). The glass vial insert was loaded into a reactor and the reactor was closed. The atmosphere in the reactor was replaced with hydrogen and pressurized to 830 psig (5824 kPa) at room temperature. The reactor was heated to 80° C. and maintained at 80° C. for 5 hours while vials were shaken. After 5 hours, the shaking was stopped, and the reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 1.

TABLE 1

| Entry | Catalyst Amt (mg) | Support | Supplier | Adipic Acid Conversion (%) | 1,6-Hexanediol Yield (%) |
|---|---|---|---|---|---|
| 1 | 9 | Zeolite CP 811C-300 | Zeolyst | 100 | 64 |
| 2 | 11 | Zeolite HSZ-390 HUA | Tosoh | 100 | 66 |

Example 2: Adipic Acid to 1,6-Hexanediol using Pt/Mo and Rh/Mo Catalysts

Suitably concentrated aqueous solutions of $Pt(NO_3)_2$ with/without $(NH_4)_6Mo_7O_{24}$ or $Rh(NO_3)_3$ with/without $(NH_4)_6Mo_7O_{24}$ were added to approximately 10 mg of solids and agitated to impregnate the supports. The samples were dried in an oven at 60° C. overnight under a dry air purge. The samples were reduced at 350° C. under forming gas (5% $H_2$ and 95% $N_2$) atmosphere for 3 hours with 5° C./min temperature ramp rate.

These catalysts were tested for adipic acid reduction using the following catalyst testing protocol. Catalyst (ca. 10 mg) was weighed into a glass vial insert followed by addition of an aqueous adipic acid solution (200 μl of 0.4 M). The glass vial insert was loaded into a reactor and the reactor was closed. The atmosphere in the reactor was replaced with hydrogen and pressurized to 750 psig (5272 kPa) at room temperature. The reactor was heated to 120° C. and maintained at 120° C. for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 2.

Example 3: Adipic Acid to 1,6-Hexanediol using Pt/W and Pt/Mo Catalysts

Suitably concentrated aqueous solutions of $(NH_4)_{10}W_{12}O_{41}$ or $(NH_4)_6Mo_7O_{24}$ were added to approximately 200 mg of solids and agitated to impregnate the supports. The samples were dried in an oven at 60° C. overnight under a dry air purge. The samples were calcined at 650° C. under air atmosphere for 3 hours with 5° C./min temperature ramp rate. Suitably concentrated aqueous solutions of $Pt(NO_3)_2$ were added to approximately 200 mg of solids and agitated to impregnate the supports. The samples were dried in an oven at 60° C. overnight under a dry air purge followed by reduction at 350° C. under forming gas (5% $H_2$ and 95% $N_2$) atmosphere for 3 hours with 5° C./min temperature ramp rate. The final catalysts were composed of ca. 3.9 wt. % Pt and 0.7 wt. % W or 3.9 wt. % Pt and 0.4 wt. % Mo, each on a silica support.

These catalysts were tested for adipic acid reduction using the following catalyst testing protocol. Catalyst was weighed into a glass vial insert followed by addition of a hot aqueous adipic acid solution (200 μl of 0.8 M). The glass vial insert was loaded into a reactor and the reactor was closed. The atmosphere in the reactor was replaced with hydrogen and pressurized to 670 psig (4721 kPa) at room temperature. The reactor was heated to 120° C. and maintained at 120° C. for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 3.

TABLE 2

| Entry | Metal 1 | Metal 2 | Support | Supplier | Adipic Acid Conversion (%) | 1,6-Hexanediol Yield (%) |
|---|---|---|---|---|---|---|
| 1 | 3.9 wt % Pt | 1.9 wt % Mo | Silica Caraict Q-10 | Fuji Silysia | 93 | 58 |
| 2 | 3.9 wt % Pt | 1.0 wt % Mo | Silica Caraict Q-10 | Fuji Silysia | 100 | 66 |
| 3 | 3.9 wt % Pt | 0.6 wt % Mo | Silica Caraict Q-10 | Fuji Silysia | 100 | 69 |
| 4 | 3.9 wt % Pt | 0.4 wt % Mo | Silica Caraict Q-10 | Fuji Silysia | 100 | 79 |
| 5 | 3.9 wt % Pt | 0.2 wt % Mo | Silica Caraict Q-10 | Fuji Silysia | 100 | 63 |
| 6 | 3.9 wt % Pt | 0.1 wt % Mo | Silica Caraict Q-10 | Fuji Silysia | 74 | 18 |
| 7 | 3.9 wt % Pt | — | Silica Caraict Q-10 | Fuji Silysia | 3 | 0 |
| 8 | 2.1 wt % Rh | 1.9 wt % Mo | Silica Caraict Q-10 | Fuji Silysia | 76 | 16 |
| 9 | 2.1 wt % Rh | 1.0 wt % Mo | Silica Caraict Q-10 | Fuji Silysia | 83 | 24 |
| 10 | 2.1 wt % Rh | 0.6 wt % Mo | Silica Caraict Q-10 | Fuji Silysia | 91 | 38 |
| 11 | 2.1 wt % Rh | 0.4 wt % Mo | Silica Caraict Q-10 | Fuji Silysia | 100 | 64 |
| 12 | 2.1 wt % Rh | 0.2 wt % Mo | Silica Caraict Q-10 | Fuji Silysia | 100 | 58 |
| 13 | 2.1 wt % Rh | 0.1 wt % Mo | Silica Caraict Q-10 | Fuji Silysia | 85 | 23 |
| 14 | 2.1 wt % Rh | — | Silica Caraict Q-10 | Fuji Silysia | 3 | 0 |

TABLE 3

| Entry | Catalyst Amt (mg) | Metal | Support | Supplier | Adipic Acid Conversion (%) | 1.6-Hexanediol Yield (%) |
|---|---|---|---|---|---|---|
| 1 | 40 | Pt—W | Silica Caraict Q-10 | Fuji Silysia | 100 | 88 |
| 2 | 20 | Pt—Mo | Silica Caraict Q-10 | Fuji Silysia | 100 | 79 |

Example 4: Adipic Acid to 1,6 Hexanediol using Pt on a Tungstated ZrO$_2$ Support A tungstated support, Zirconia Z-2087 (Daiichi Kigenso Kagaku Kogyo) (about 7.68 wt. % W, balance essentially ZrO$_2$; hafnium is commonly an impurity in this oxide) was dried in an oven at 60° C. overnight under a dry air purge. The substrate was then calcined at 650° C. under air atmosphere for 3 hours with 5° C./min temperature ramp rate.

A suitably concentrated aqueous solution of Pt(NO$_3$)$_2$ was added to 10 mg of the support and agitated to impregnate the same. The sample was dried in an oven at 60° C. overnight under a dry air purge. Thereafter, the sample was reduced at 350° C. under forming gas (5% H$_2$ and 95% N$_2$) atmosphere for 3 hours with 5° C./min temperature ramp rate. The final catalysts were composed of ca. 15.6 wt. % Pt on the tungstated ZrO$_2$ support.

These catalysts were tested for adipic acid reduction using the following catalyst testing protocol. Catalyst (ca. 10 mg) was weighed into a glass vial insert followed by addition of an aqueous adipic acid solution (200 μl of 0.4 M). The glass vial insert was loaded into a reactor and the reactor was closed. The atmosphere in the reactor was replaced with hydrogen and pressurized to 750 psig (5272 kPa) at room temperature. The reactor was heated to 120° C. and maintained at 120° C. for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 4.

TABLE 4

| Entry | Catalyst Amt (mg) | Metal | Support | Supplier | Adipic Acid Conversion (%) | 1.6-Hexanediol Yield (%) |
|---|---|---|---|---|---|---|
| 1 | 10 | Pt | Zirconia Z-2087(W) | DKKK | 100 | 63 |

Example 5: Adipic Acid to 1,6-Hexanediol using Pt/W Catalysts

Suitably concentrated aqueous solutions of (NH$_4$)$_{10}$W$_{12}$O$_{41}$ were added to approximately 10 mg of solids and agitated to impregnate the supports. The samples were dried in an oven at 60° C. overnight under a dry air purge. The samples were calcined at 650° C. under air atmosphere for 3 hours with 5° C./min temperature ramp rate. Suitably concentrated aqueous solutions of Pt(NO$_3$)$_2$ were added to approximately 10 mg of solids and agitated to impregnate the supports. The samples were dried in an oven at 60° C. overnight under a dry air purge followed by reduction at 350° C. under forming gas (5% H$_2$ and 95% N$_2$) atmosphere for 3 hours with 5° C./min temperature ramp rate.

These catalysts were tested for adipic acid reduction using the following catalyst testing protocol. Catalyst (ca. 10 mg) was weighed into a glass vial insert followed by addition of an aqueous adipic acid solution (200 μl of 0.4 M). The glass vial insert was loaded into a reactor and the reactor was closed. The atmosphere in the reactor was replaced with hydrogen and pressurized to 750 psig (5272 kPa) at room temperature. The reactor was heated to 120° C. and maintained at 120° C. for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 5.

TABLE 5

| Entry | Metal 1 | Metal 2 | Support | Supplier | Adipic Acid Conversion (%) | 1.6-Hexanediol Yield (%) |
|---|---|---|---|---|---|---|
| 1 | 3.9 wt % Pt | 3.7 wt % W | Silica Caraict Q-10 | Fuji Silysia | 23 | 7 |
| 2 | 3.9 wt % Pt | 2.2 wt % W | Silica Caraict Q-10 | Fuji Silysia | 87 | 36 |
| 3 | 3.9 wt % Pt | 1.5 wt % W | Silica Caraict Q-10 | Fuji Silysia | 87 | 41 |
| 4 | 3.9 wt % Pt | 0.7 wt % W | Silica Caraict Q-10 | Fuji Silysia | 92 | 62 |
| 5 | 3.9 wt % Pt | 0.4 wt % W | Silica Caraict Q-10 | Fuji Silysia | 91 | 52 |

Example 6: Adipic Acid to 1,6-Hexanediol using Pt/W Catalysts

Approximately 30 g of a zirconia hydroxide-silicon dioxide material was calcined at 800° C. under air atmosphere for 3 hours with 5° C./min temperature ramp rate. A suitably concentrated aqueous solution of $(NH_4)_{10}W_{12}O_{41}$ was added to approximately 20 g of calcined solid and agitated to impregnate the support. The sample was dried in an oven at 60° C. overnight under a dry air purge. The sample was calcined at 600° C. under air atmosphere for 3 hours with 5° C./min temperature ramp rate. A Suitably concentrated aqueous solution of $Pt(NO_3)_2$ were added to the solid and agitated to impregnate the support. The sample was dried in an oven at 60° C. overnight under a dry air purge followed by reduction at 350° C. under forming gas (5% $H_2$ and 95% $N_2$) atmosphere for 3 hours with 5° C./min temperature ramp rate. The final catalysts were composed of ca. 3.9 wt. % Pt and 3.7 wt. % W.

The catalyst was tested for adipic acid reduction using the following catalyst testing protocol. Catalyst was weighed into a glass vial insert followed by addition of a hot aqueous adipic acid solution (200 μl of 0.8 M). The glass vial insert was loaded into a reactor and the reactor was closed. The atmosphere in the reactor was replaced with hydrogen and pressurized to 670 psig (4721 kPa) at room temperature. The reactor was heated to 120° C. and maintained at 120° C. for 150 minutes while vials were shaken. After 150 minutes, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 6.

TABLE 6

| Entry | Catalyst Amt mg) | Metal | Support | Supplier | Adipic Acid Conversion (%) | 1.6-Hexanediol Yield (%) |
|---|---|---|---|---|---|---|
| 1 | 40 | Pt—W | Zirconia FZO 2264 | MEL Chemical | 100 | 83 |

We claim:

1. A process for preparing 1,6-hexanediol, the process comprising:

reacting an adipic acid substrate and hydrogen in the presence of a heterogeneous catalyst comprising a first metal selected from the group consisting of Pt, Rh, and mixtures thereof and a second metal selected from the group consisting of Mo, W, and mixtures thereof to convert at least a portion of the adipic acid substrate to 1,6-hexanediol, wherein the adipic acid substrate is a compound of formula I:

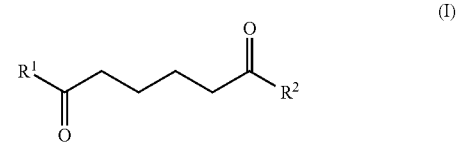

wherein each $R^1$ and $R^2$ is independently hydroxyl or $OR^a$ each $R^a$ is independently selected from the group consisting of alkyl and a salt-forming ion;
the reaction is carried out at a temperature in the range of from 40° C. to 200° C.; and
wherein the molar ratio of the first metal to the second metal (M1:M2) is in the range of from 10:1 to 2:1.

2. The process of claim 1, wherein reacting the adipic acid substrate with hydrogen in the presence of the heterogeneous catalyst comprises any one of the following:
a) combining the adipic acid substrate, heterogeneous catalyst, and a solvent and contacting the combined adipic acid substrate, heterogeneous catalyst, and solvent with hydrogen; or
b) combining the adipic acid substrate and a solvent and contacting the combined adipic acid substrate and solvent with a heterogeneous catalyst and hydrogen; or
c) contacting the heterogeneous catalyst with hydrogen and adding the adipic acid substrate and a solvent to the heterogeneous catalyst contacted with hydrogen.

3. The process of claim 1, wherein reacting the adipic acid substrate with hydrogen in the presence of the heterogeneous catalyst comprises any one of the following:
a) combining the adipic acid substrate, heterogeneous catalyst, and a solvent at a temperature in the range of from about 20° C. to about 200° C. and contacting with hydrogen the combined adipic acid substrate, heterogeneous catalyst, and solvent; or
b) contacting the heterogeneous catalyst with a solvent at a temperature in the range of from about 20° C. to about 200° C. and contacting the heterogeneous catalyst and solvent with the adipic acid substrate and hydrogen.

4. The process of claim 2 wherein the solvent is selected from the group of water, ethers, alcohols which do not react with the adipic acid substrate, and mixtures thereof.

5. The process of claim 1, wherein reacting the adipic acid substrate with hydrogen in the presence of the heterogeneous catalyst and solvent comprises:

a) contacting the adipic acid substrate with water; and,
b) contacting the adipic acid substrate and water with a solvent, hydrogen, and catalyst.

6. The process of claim 1, wherein, each $R^a$ is independently selected from the group consisting of $C_1$-$C_{18}$ alkyl and salt-forming ion.

7. The process of claim 1, wherein the salt-forming ion is selected from the group consisting of ammonium ions, alkali metal ions, and alkaline earth metal ions.

8. The process of claim 1, wherein the reaction is carried out at a temperature in the range of from about 70° C. to about 180° C.

9. The process of claim 1, wherein the reaction is carried out at a pressure in the range of from about 650 psig (4583 kPa) to about 1250 psig (8720 kPa) and a temperature in the range of from about 70° C. to about 180° C.

10. The process of claim 1, wherein the reaction is carried out at a partial pressure of hydrogen in the range of from about 650 psi (4482 kPa) to about 1250 psi (8,618 kPa) and a temperature in the range of from about 70° C. to about 180° C.

11. The process of claim 1, wherein the yield of 1,6-hexanediol is at least about 60%.

12. The process of claim 1, wherein the mass ratio of adipic acid substrate to the first metal (M1) is at least about 1:1.

13. The process of claim 1, wherein the mass ratio of adipic acid substrate to the first metal (M1) is in the range of from about 1:1 to about 1000:1.

14. The process of claim 1, wherein the mass ratio of adipic acid substrate to the second metal (M2) is at least about 5:1.

15. The process of claim 1, wherein mass ratio of adipic acid substrate to the second metal (M2) is in the range of from about 5:1 to about 2000:1.

16. The process of claim 1, wherein the mass ratio of adipic acid substrate to the total mass of the first and second metals (M1+M2) is at least about 1:1.

17. The process of claim 1, wherein the mass ratio of adipic acid substrate to the total mass of the first and second metals (M1+M2) is in the range from about 1:1 to about 1500:1.

18. The process of claim 1, wherein the adipic acid substrate and hydrogen are reacted in the presence of a heterogeneous catalyst in a fixed bed reactor.

19. The process of claim 1, wherein the first metal comprises Rh and the second metal comprises Mo.

20. The process of claim 1, wherein the first metal comprises Rh and the second metal comprises W.

21. A process for preparing 1,6-hexanediol, the process comprising:

reacting an adipic acid substrate and hydrogen in the presence of a heterogeneous catalyst comprising a first metal comprising Pt and a second metal comprising Mo to convert at least a portion of the adipic acid substrate to 1,6-hexanediol, wherein the adipic acid substrate is a compound of formula I:

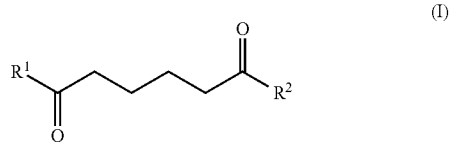

(I)

wherein each $R^1$ and $R^2$ is independently hydroxyl or $OR^a$
each $R^a$ is independently selected from the group consisting of alkyl and a salt-forming ion;
the reaction is carried out at a temperature in the range of from 40° C. to 200° C.; and
wherein the molar ratio of the first metal to the second metal (M1:M2) is in the range of from about 10:1 to about 2:1.

22. A process for preparing 1,6-hexanediol, the process comprising:

reacting an adipic acid substrate and hydrogen in the presence of a heterogeneous catalyst comprising a first metal comprising Pt and a second metal comprising W to convert at least a portion of the adipic acid substrate to 1,6-hexanediol, wherein the adipic acid substrate is a compound of formula I:

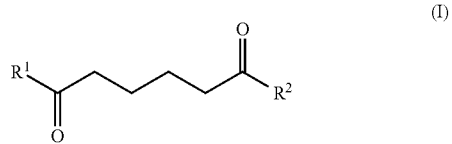

(I)

wherein each $R^1$ and $R^2$ is independently hydroxyl or $OR^a$
each $R^a$ is independently selected from the group consisting of alkyl and a salt-forming ion;
the reaction is carried out at a temperature in the range of from 40° C. to 200° C.; and
wherein the molar ratio of the first metal to the second metal (M1:M2) is in the range of from about 10:1 to about 2:1.

* * * * *